US00PP25624P2

(12) United States Plant Patent
Delabroye

(10) Patent No.: US PP25,624 P2
(45) Date of Patent: Jun. 16, 2015

(54) ***HEUCHERA* PLANT NAMED 'MUSCAT'**

(50) Latin Name: ***Heuchera* hybrid**
Varietal Denomination: Muscat

(71) Applicant: Thierry Delabroye, Hantay (FR)

(72) Inventor: Thierry Delabroye, Hantay (FR)

(73) Assignee: Sandrine Delabroye, Hantay (FR)

( * ) Notice: Subject to any disclaimer, the term of this patent is extended or adjusted under 35 U.S.C. 154(b) by 96 days.

(21) Appl. No.: 13/694,449

(22) Filed: Dec. 4, 2012

(51) Int. Cl.
*A01H 5/12* (2006.01)

(52) U.S. Cl.
USPC ..... Plt./440

(58) Field of Classification Search
USPC ..... Plt./440
CPC ..... A01H 5/02; A01H 5/12; A01H 5/00; A01H 5/025
See application file for complete search history.

(56) References Cited

PUBLICATIONS

Gabot Plantarium 2011: Viele Neuheiten, retrieve on Jul. 17, 2014, retrieved from the Internet at <http://www.gabot.de/index.php/News-Details/52/0/?&tx_ttnews%5Btt_news%5D=218168tx_ttnews%5BbackPid%5D=1&cHash=6cffc84d7d> 9 pp.*
Plantagogo *Heuchera* 'Muscat' retrieved on Jul. 17, 2014, retrieved from the Internet at <http://www.plantagogo.com/acatalog/HEUCHERA----Muscat---PBR-805.html> 2pp.*
Google English translation of Gabot Plantarium 2011: Viele Neuheiten, 12 pp.*

* cited by examiner

*Primary Examiner* — June Hwu
(74) *Attorney, Agent, or Firm* — Penny J. Aguirre

(57) ABSTRACT

A new cultivar of hybrid *Heuchera* named 'Muscat', characterized by its uniquely colored foliage with leaves that are green with a silvery overlay between the veins with newer leaves lighter green in color, its leaves that are relatively flat in aspect (not ruffled), its tolerance to heat and humidity, its compact and upright plant habit, its pink flowers, and its cold hardiness in Zones U.S.D.A Zone 3 to 8.

2 Drawing Sheets

Botanical classification: *Heuchera* hybrid.
Cultivar designation: 'Muscat'.

CROSS REFERENCE TO A RELATED APPLICATION

This application is co-pending with a U.S. Plant Patent Application filed for a plant derived from the same breeding program that is entitled *Heuchera* Plant Named 'Pinot Bianco' (U.S. Plant patent application Ser. No. 13/694,458).

BACKGROUND OF THE INVENTION

The present invention relates to a new and distinct cultivar of *Heuchera* of hybrid origin, botanically known as a *Heuchera* and is hereinafter referred to by its cultivar name 'Muscat'.

The new cultivar arose from a cross made by the Inventor in 2008 between 'Citronelle' as the female parent (U.S. Plant Pat. No. 17,934) and 'Pinot Gris' as the male parent (U.S. Plant Pat. No. 19,592). The Inventor selected 'Muscat' in 2009 as a single unique plant amongst the seedlings that resulted from the above cross.

Asexual propagation of the new cultivar was first accomplished by the Inventor by division in Hantay, France in 2011. Asexual propagation of the new cultivar by division and tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Muscat' as a new and unique cultivar of *Heuchera*.

1. 'Muscat' exhibits uniquely colored foliage with leaves that are green with a silvery overlay between the veins with newer leaves lighter green in color.
2. 'Muscat' exhibits leaves that are relatively flat in aspect (not ruffled).
3. 'Muscat' is tolerant to heat and humidity imparted by having *Heuchera*×*villosa* in its parentage.
4. 'Muscat' exhibits a compact and upright plant habit.
5. 'Muscat' exhibits a vigorous growth habit.
6. 'Muscat' exhibits deep pink flowers.
7. 'Muscat' is hardy in U.S.D.A. Zones 3 to 8.

'Muscat' is a unique *Heuchera* with foliage coloration that is unknown to exist in other cultivars of *Heuchera* known to the Inventor.

'Muscat' can be compared most closely to 'Citronelle' (U.S. Plant Pat. No. 17,934), 'Pistache' (U.S. Plant Pat. No. 19,585), 'Pinot Gris' and 'Pinot Bianco' in having some similarity in foliage color and form and in having *Heuchera*× *villosa* in its parentage. 'Citronelle' differs from 'Muscat' in having yellow-green foliage without distinct colored veins and lacking a silvery overlay. 'Pistache' differs from 'Muscat' in having lime-green foliage without distinct colored veins and lacking a silver overlay. 'Pinot Gris' differs from 'Muscat' in having foliage that emerges orange-yellow with a silver overlay and changes to a rosy grayed red with a silver overlay in summer. 'Pinot Bianco' differs in having lighter green foliage with a silver overlay and in having bronze-red coloration on the lower leaf surface.

BRIEF DESCRIPTION OF THE DRAWING

The accompanying colored photographs illustrate the overall appearance and distinct characteristics of the new

*Heuchera*. The photographs were taken of a plant two years in age as grown outdoors in a 7.5-liter container.

Figure 1:
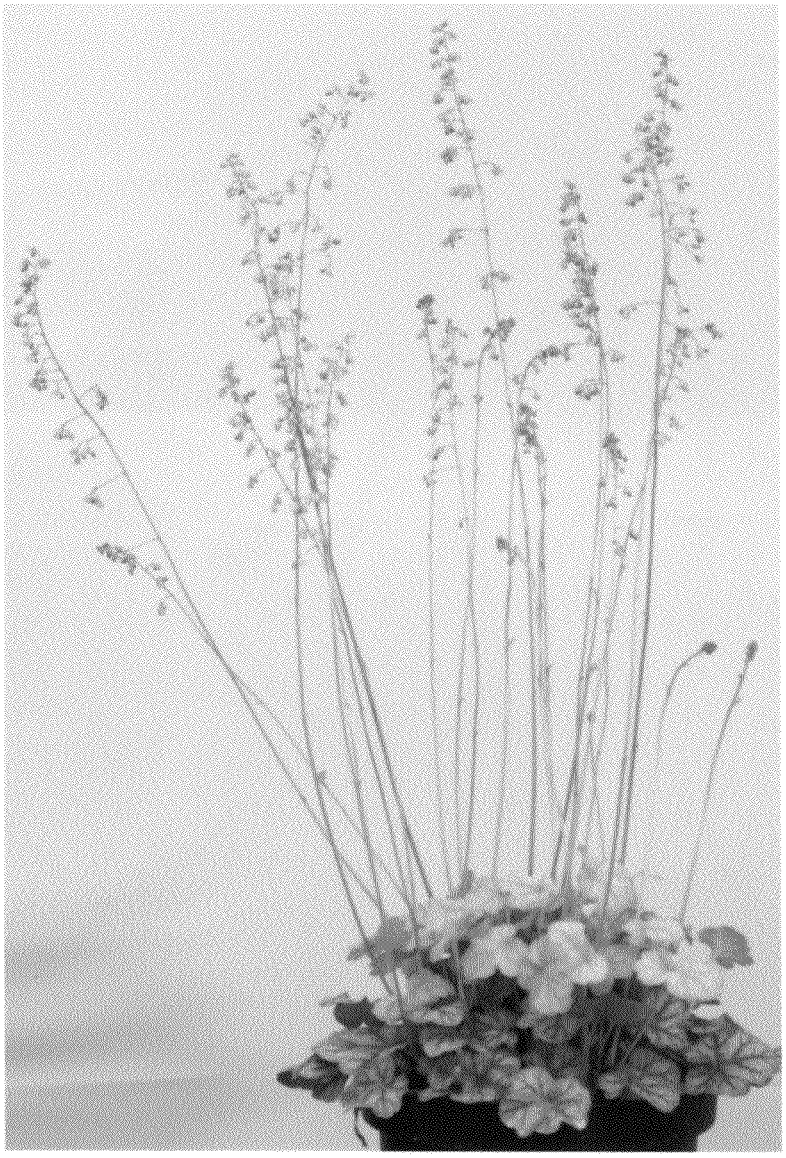

The photograph in FIG. 1 provides a view of the plant habit and typical spring coloration of the foliage of 'Muscat' in bloom.

Figure 2:
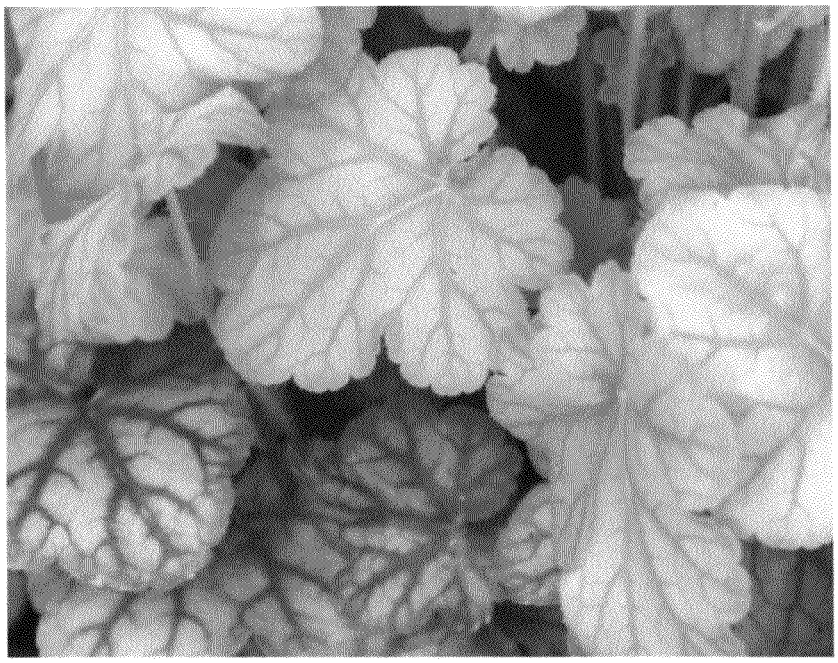

The photograph in FIG. 2 provides a close-up view of the foliage of 'Muscat'.

Figure 3:
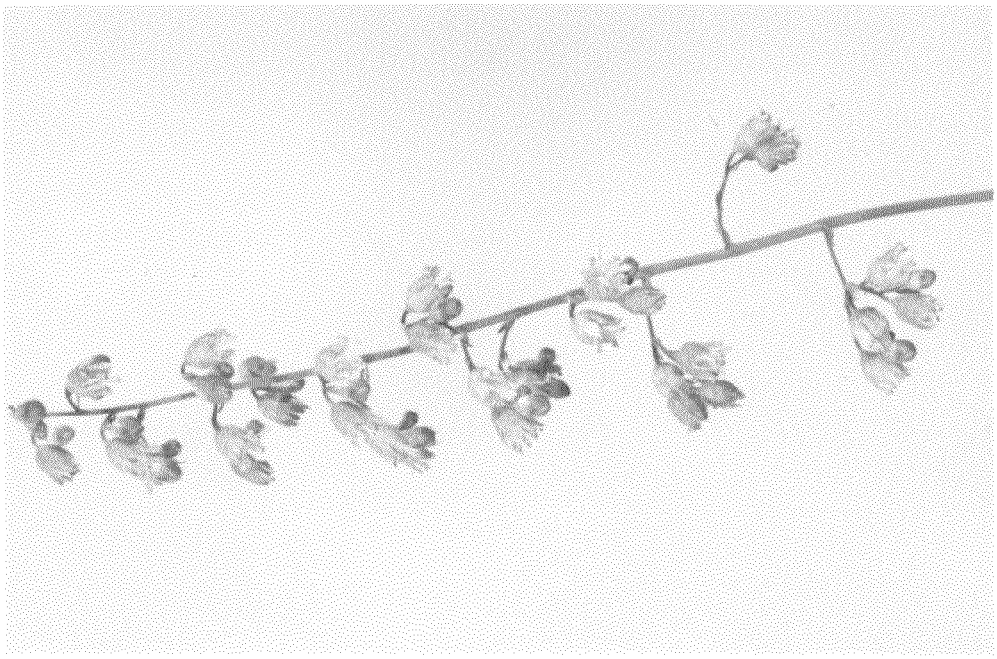

The photograph in FIG. 3 provides a close-up view of the flowers of 'Muscat'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 2-year-old plants of the new cultivar as grown outdoors in 7.5-liter containers in The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Early to mid spring in The Netherlands.

*Plant type.*—Herbaceous perennial.

*Plant habit.*—Compact, clump-forming upright mounded foliage.

*Height and spread.*—Average of 20 cm in height from soil to top of leaves, 77.6 cm from soil to top of inflorescences, and about 40 cm in width.

*Hardiness.*—At least in U.S.D.A. Zones 3 to 8.

*Diseases and pests.*—Not more susceptible to pests and diseases than other *Heuchera* varieties.

*Root description.*—Fibrous roots on woody rootstalks.

*Branching habit.*—Basal rosette, no lateral branches, only flowering stems growing from rosettes.

*Basal branching.*—No lateral stems only flowering stems.

*Propagation.*—In vitro propagation is the preferred method, division is also possible.

*Growth rate.*—Vigorous.

Stem description (flowering stem or main peduncle):

*Shape.*—Round.

*Stem color.*—Blend of 144A and 146B.

*Stem size.*—An average of 2 mm in diameter and 51 cm in length.

*Stem strength.*—Strong.

*Stem aspect.*—Flowering stems grow in an average angle of 80° to base (0°=horizontal).

*Stem surface.*—Moderately glossy, rounded, densely covered with short hairs an average of 1 mm in length and NN155D in color.

*Stem number.*—Average of 27 flowering stems, average of 3 per rosette.

*Branching* .—None.

Foliage description:

*Leaf shape.*—Orbicular.

*Leaf division.*—Simple.

*Leaf base.*—Hastate, slightly overlapping.

*Leaf apex.*—Rounded.

*Leaf venation.*—Laciniate.

*Leaf margins.*—Lobed with average of 5 lobes per leaf, lobe margins crenate.

*Leaf attachment.*—Petiolate.

*Leaf arrangement.*—Alternate, basal rosettes.

*Leaf orientation.*—Typically nearly horizontal to petiole.

*Leaf surface.*—Both surfaces dull and moderately covered with short hairs, 1 mm in length and NN155D in color.

*Leaf color.*—Young upper surface; 145C, area near veins become 144C to 145A, veins N144B, young lower surface; 145B, mature upper surface; between 148D and 194B, area near the veins become 147A to 147B, mature lower surface; 148C.

*Leaf size.*—Average of 6.8 cm in length and 6.8 cm in width.

*Leaf quantity.*—15 per basal rosette.

*Vein color.*—Upper side; 144C, lower side; 148C, tinged with 182C.

*Petioles.*—Round in shape, average of 9.1 cm in length and 2 mm in width, color; 144A, surface is villose.

*Stipules.*—Small leafy stipules at the base of each leaf, narrow acute apex, with an average of 1.3 cm in length and 3 mm in width and 182D in color, surface is villose.

Flower description:

*Inflorescence type.*—Numerous small bell-shaped flowers arranged on pyramidal panicles on flower scapes emerging from the base of the rosette.

*Inflorescence size.*—An average of 17.8 cm in height (excluding peduncle) and about 4.8 cm in width.

*Inflorescence number.*—An average of 27 (7.5 liter container).

*Flower fragrance.*—None.

*Flower quantity.*—Average of 60 flowers per flowering stem.

*Flower lastingness.*—Average of one week.

*Flower buds.*—Obovate in shape, an average of 4.5 mm in length and 2 mm in diameter, color is between N57A and 58B.

*Flower aspect.*—Drooping to slightly outward.

*Flower type.*—Campanulate.

*Flower size.*—About 7 mm in depth (height) and 6 mm in diameter.

*Petals.*—About 5, rotate arrangement and implanted in the hypanthium at the lower half of the calyx, petals and filaments are fused, linear in shape, margin is entire, apex is narrowly acute, upper and lower surface is dull and smooth, color of upper and lower surface when opening and mature is 68B, about 4 mm in length and 1 mm in width.

*Calyx.*—Campanulate, 7 mm in length and 6 mm in diameter.

*Sepals.*—Campanulate hypanthium, 5, fused into hypanthium, elliptic in shape, about 7 mm in length and 2 mm in width, margin is entire, apex is broadly acute, fused base, color: immature upper surface; 63C, tip 58D, immature lower surface; 58B, base 58C to 58D, mature upper surface; 63C, tip 63B, mature lower surface; 58C, base 58D.

*Bracts.*—1, at base of pedicels, lanceolate in shape, a blend ranging between 144A and 146B and 68B in color, about 4 mm in length and 1 mm in width, acute, base truncate.

*Peduncles.*—Rachis; average of 16.9 cm in length and 1 mm in width, moderate strength, held at a 0° angle (straight on top of flowering stem), color of both surfaces; 144A, secondary peduncles; average of 1.5 cm in length, 0.75 mm in diameter, moderate in strength, held at a 85° (0°=straight upright) to rachis, color of both surfaces; 144A, surfaces are moderately glossy, rounded, densely covered with short hairs an average of 1 mm in length and NN155D in color.

*Pedicels.*—Average of 2 mm in length and 0.5 mm in width, moderate strength, color 177A to 177B, pedicel of primary flower of each spikelet straight on top of secondary pedicel, pedicels of secondary and tertiary flowers of each spikelet in an average angle of 45° (0°=straight on top of secondary peduncle), surfaces is moderately glossy, rounded, densely covered with short hairs an average of 1 mm in length and NN155D in color.

Reproductive organs:

*Gynoecium.*—2 pistils, pointed in shape, about 4 mm in length, and 157D in color, styles are 3.75 mm in length and NN155D in color, ovaries are 145D in color.

*Androcoecium.*—5 stamens, anthers are ovate in shape, 0.5 mm and 165A in color, filament is 4 mm in length and N155B in color, pollen is moderate in quantity and 163B in color.

*Seed/fruit.*—No fruit or seeds detected to date.

It is claimed:

1. A new and distinct cultivar of hybrid *Heuchera* plant named 'Muscat' as herein illustrated and described.

* * * * *